(12) United States Patent
Henniges et al.

(10) Patent No.: US 8,506,518 B2
(45) Date of Patent: Aug. 13, 2013

(54) TIP ASSEMBLY FOR A MEDICAL/SURGICAL IRRIGATOR, THE TIP ASSEMBLY INCLUDING A RESERVOIR FOR HOLDING A THERAPEUTIC AGENT AND A PUMP FOR DISCHARGING THE AGENT

(75) Inventors: Bruce Henniges, Galesburg, MI (US); Richard F. Huyser, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 13/416,007

(22) Filed: Mar. 9, 2012

(65) Prior Publication Data

US 2013/0066261 A1   Mar. 14, 2013

Related U.S. Application Data

(60) Division of application No. 12/306,268, filed on Dec. 23, 2008, now Pat. No. 8,137,306, which is a continuation of application No. PCT/US2007/072774, filed on Jul. 3, 2007.

(60) Provisional application No. 60/818,639, filed on Jul. 5, 2006.

(51) Int. Cl.
*A61N 1/30* (2006.01)

(52) U.S. Cl.
USPC .............................. 604/19; 604/82

(58) Field of Classification Search
USPC ...................... 604/39–40, 43, 82, 87, 19, 118
See application file for complete search history.

(56) References Cited

U.S. PATENT DOCUMENTS

| | | | |
|---|---|---|---|
| 4,601,709 A | 7/1986 | Kabbay | |
| 5,470,305 A | 11/1995 | Arnett et al. | |
| 6,030,215 A | 2/2000 | Ellion et al. | |
| 6,083,189 A * | 7/2000 | Gonon et al. | 604/19 |
| 6,156,004 A * | 12/2000 | Tremaine et al. | 604/27 |
| 6,200,292 B1 * | 3/2001 | French et al. | 604/131 |
| 6,471,668 B2 | 10/2002 | Henniges et al. | |
| 6,561,803 B1 | 5/2003 | Rizoiu et al. | |
| 6,595,968 B1 | 7/2003 | Perrino | |
| 6,684,753 B1 | 2/2004 | Urrutia | |
| 6,878,142 B2 * | 4/2005 | Lawrence et al. | 604/540 |
| 2002/0058914 A1 | 5/2002 | Henniges et al. | |
| 2005/0148954 A1 * | 7/2005 | Abell | 604/276 |
| 2008/0154183 A1 * | 6/2008 | Baker et al. | 604/28 |
| 2010/0016787 A1 * | 1/2010 | Shapiro et al. | 604/31 |

FOREIGN PATENT DOCUMENTS

| | | |
|---|---|---|
| FR | 2873172 A1 | 1/2006 |
| WO | 98/30270 A | 7/1988 |
| WO | 02/074363 A2 | 9/2002 |
| WO | 2005/070480 A | 8/2005 |

OTHER PUBLICATIONS

European Patent Office, , "PCT App. No. PCT/US2007/072774 Int'l. Srch Rpt & ISA Wrtn Opinion", Apr. 2008, 18 pages.

* cited by examiner

*Primary Examiner* — Nicholas Lucchesi
*Assistant Examiner* — Melissa A Snyder (57) ABSTRACT

A medical/surgical irrigator with a handpiece for discharging a lavage solution. There is reservoir in which a therapeutic agent is stored. The therapeutic agent can be selectively mixed with the lavage solution to form a blended solution. The mixing can be performed selectively so as to make it possible to sequentially apply the blended solution or a basic (lavage only) solution.

18 Claims, 8 Drawing Sheets

TIP ASSEMBLY FOR A MEDICAL/SURGICAL IRRIGATOR, THE TIP ASSEMBLY INCLUDING A RESERVOIR FOR HOLDING A THERAPEUTIC AGENT AND A PUMP FOR DISCHARGING THE AGENT

CROSS-REFERENCE TO RELATED APPLICATIONS

This application is a divisional of U.S. patent application Ser. No. 12/306,268, filed 23 Dec. 2008, now U.S. Pat. No. 8,137,306. application Ser. No. 12/306,268 is a continuation of PCT Application Serial No. PCT/US2007/072774, filed 3 Jul. 2007, which claims the benefit of U.S. Provisional Patent Application Ser. No. 60/818,639, filed 5 Jul. 2006, both of which are hereby incorporated by reference in their entireties.

FIELD OF THE INVENTION

This invention is generally related to a system and method for discharging a lavage solution to a target site on or in the body. More particularly this invention is directed to a system and method for discharging a lavage solution, wherein, as part of the discharge process, a therapeutic agent is selectively blended into the lavage solution so as to result in the discharge of a lavage solution that provides the benefit of the therapeutic agent.

BACKGROUND OF THE INVENTION

The Applicant's Assignee's U.S. Pat. No. 5,470,305, issued 28 Nov. 1995, and U.S. Pat. No. 6,471,668, issued 29 Oct. 1992, both of which are incorporated herein by reference, disclose medical/surgical lavage devices. This type of device is generally in the form of a handpiece that includes pump that discharges a pulsed flow of irrigation solution at a body site to be cleaned. Typically, the lavage solution is discharged from the handpiece through a tip assembly to a target site on the body. It is further known to provide a suction line that extends from the tip assembly. Thus, a typical lavage device is designed to deliver a charge of solution at the target site. Then, the solution is drawn away from the site through the attached suction line.

Often, the irrigation solution is either sterile water or a saline solution. The solution is typically stored in a collapsible closed container with flexible walls. Often the container is a transparent bag.

The above devices are useful for cleaning wound sites. Lavage units are also used to remove debris and extraneous tissue from around target tissue in order to allow a further procedure to be performed on the target tissue. One such type of tissue to which it is known to apply a lavage solution is bone. Specifically, the lavage solution, which is often discharged in a pulse flow, is used to clean the bone and surrounding soft tissue in order to allow a further procedure to be performed on the bone itself.

There are, however, medical procedures during which it is desirable to do something more than simply clean the tissue subject to the procedure. For example, there are some situations wherein when it is appropriate to apply an antibiotic directly to a section of exposed tissue. This procedure may be called for when there is concern that the tissue, if left untreated, would be prone to infection. Alternatively, there may be situations wherein the likelihood of the tissue becoming infecting is minimized if a cleaning agent stronger than saline is applied to the tissue. Castile soap is one such cleaning agent. Also, during the process of fitting an orthopedic implant, it may be desirable to apply a bone growth compound to the exposed surface of the bone against which the implant is to be fitted.

When it is desirable to apply such agents directly to the target tissue, a clinician may have to use plural surgical instruments. Specifically, a first instrument, such as a syringe, is used to apply the therapeutic agent. A second instrument, a suction wand, may be needed to collect the run off volume of the therapeutic agent that is not absorbed into the tissue. If the target site is one that is also subjected to lavage cleaning, a third instrument, the lavage handpiece needs to be used.

Having to provide these different instruments adds to the overall expense of performing the medical procedure. Also, having to provide each of these instruments adds to both the clutter in the operating room and the number of instruments that may need to be near simultaneously employed at the surgical site. Having to so provide these numerous instruments can add to the complexity of the surgical procedure.

To reduce this complexity, some clinicians have been known inject a therapeutic agent into the bag containing the lavage solution. The actuation of the lavage handpiece results in the discharge of a blended solution to the target site. To date, there have been some efforts to introduce antibiotics or soaps to the surgical sites by the mixing of these agents into the solution bag prior to discharge.

This mixing of the therapeutic agent directly into the solution bag does make it possible to discharge a blended solution, a solution consisting of the basic lavage solution and the therapeutic agent, directly at a target site. However, there are some disadvantages associated with this protocol. One significant limitation is that once the therapeutic agent is introduced into the solution bag, the entire contents of the bag essentially become the blended solution. There may be instances when the procedure only requires a limited application of the blended solution followed by an application of a neutral solution. In this instance, in order for the procedure to continue, the bag with the blended solution must be removed and a new bag that only contains the neutral solution substituted therefore. Having to perform these steps can increase the overall time it takes to complete the procedure. Also, having to discard the one bag and provide the new bag adds to generation of waste. If the procedure calls for the sequential application of multiple blended solutions, then the waste generated could increase arithmetically.

Further, care must be taken to, in a sterile environment ensure that the proper volume therapeutic agent is added to the solution bag. This is to ensure that the blended solution contains the appropriate proportion of the therapeutic agent. However, even when the correct volume of therapeutic agent is added to the lavage bag, it can still be difficult to ensure that the appropriate proportion of therapeutic agent is discharged from the lavage handpiece. The difficulty arises because the therapeutic agent may have a specific gravity appreciably different from that of the lavage solution. For example, if the therapeutic agent has a relatively high specific gravity, it may settle in the bottom of the lavage bag. Often, the bag is spiked, the open port created, above its base. If the therapeutic agent owing to its high specific gravity settles below this point, it may not be discharged in sufficient volume. Alternatively, if the agent settles around the opening, it may be discharged in an excessively high concentration. Difficulties can also arise discharging a therapeutic agent with a relatively low specific gravity. In this circumstance, the agent may again not mix with the solution and, instead, float to the top of the bag. If the fluids in the lavage bag so stratify again, the agent may not be discharged in the appropriate proportion in order to accomplish the desired therapeutic effect.

SUMMARY OF THE INVENTION

This invention is directed to an integrated lavage system. The lavage system of this invention is capable of discharging, in any sequence, a conventional, neutral, basic lavage solution, or one or more blended solutions each of which consists of a mixture of the basic solution and a therapeutic agent.

The lavage system of this invention consists of a handpiece and a pump. Often, but not always, the pump is disposed in the handpiece. An inlet line extends from a solution bag to the pump. When the pump is actuated, the pump forces the solution out of the bag towards the handpiece. A tip assembly extends from the handpiece. The solution is discharged from the handpiece to the target site. In one version of the integrated system of this invention, a cartridge is series connected between the inlet line and the solution bag. The cartridge contains the therapeutic agent that is to be added to the lavage solution. A mixer integral with the cartridge adds the therapeutic agent to the lavage solution as the neutral solution flows through the cartridge.

In an alternative version of this invention, the tip assembly is removably attached to the handpiece. Some of the tip assemblies include reservoirs. Each reservoir functions as void space in which a quantity of therapeutic agent is stored. Also part of the tip assembly is a discharge assembly. The discharge assembly is designed to allow the clinician to selectively introduce the therapeutic agent directly to the target site as part of the stream of the solution discharged towards the patient.

DETAILED DESCRIPTION

Figure 1:
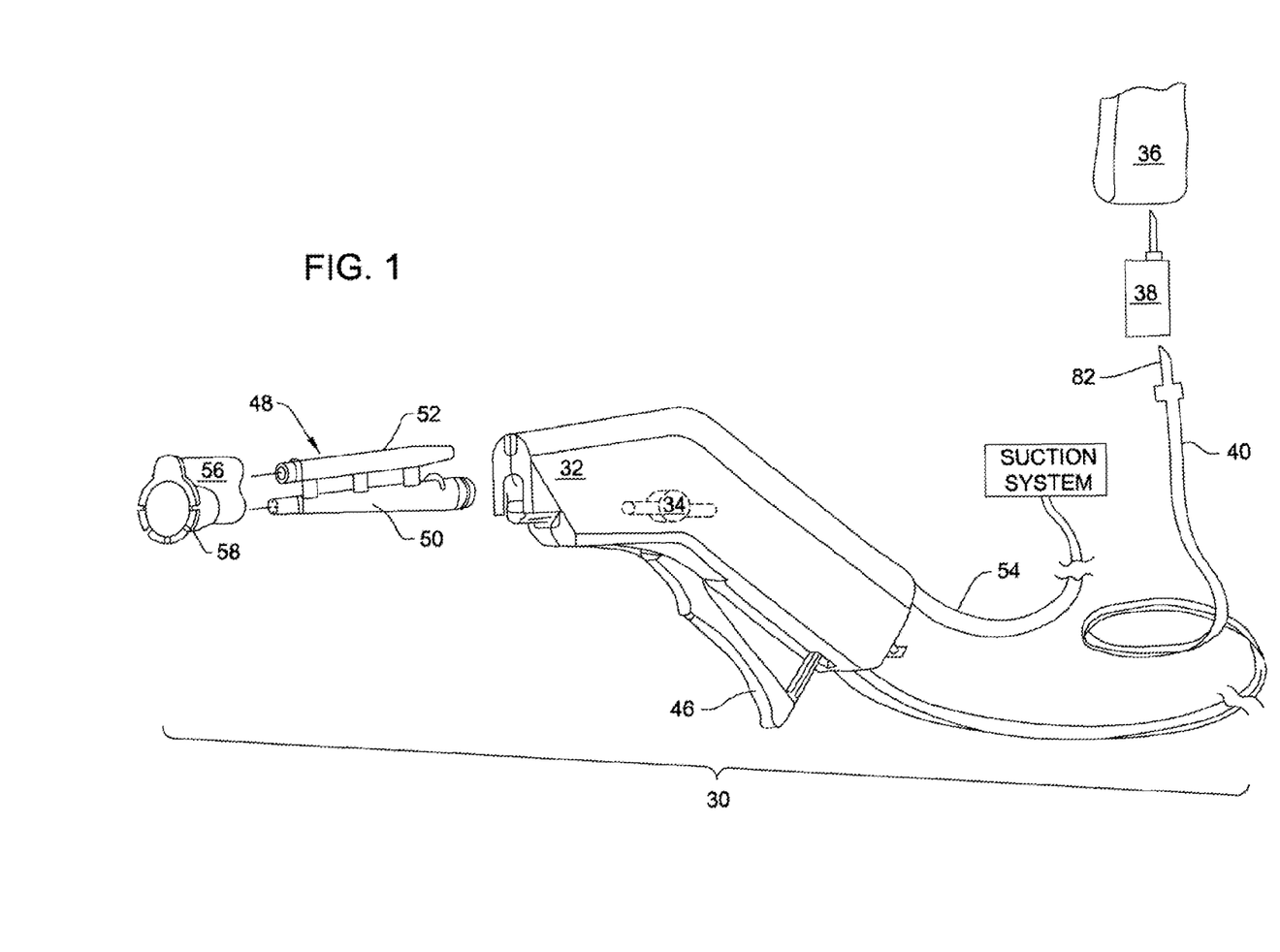
FIG. 1 depicts a basic lavage irrigator of this invention and further illustrates where a venturi unit for dispensing a therapeutic agent such as soap can be installed.

FIG. 1 illustrates an integrated lavage system 30 constructed in accordance with this invention. System 30 includes an irrigator handpiece 32. Internal to the handpiece is a pump 34 represented by a phantom cylinder. The basic solution discharged from the handpiece 32 is stored in a bag 36 remote from the handpiece. A supply tube 40 that extends from the bag 36 to the handpiece 32 serves as the conduit through which the solution is gravity flowed to the pump 34. In series between the bag 36 and supply tube 40 is a mixing cartridge 38. As described below, mixing cartridge includes a reservoir 42 and a mixing chamber 44, both seen in FIG. 2B. Reservoir 42 holds the therapeutic agent that is to be added to the basic solution stored in the bag 36. Mixing chamber 44 is a void space internal to the cartridge 38 wherein the therapeutic agent mixes with the basic solution that flows to the handpiece 32 for discharge.

A trigger 46, is pivotally attached to the handpiece 32. The trigger 46 is part of a control assembly, the remaining components of which are not illustrated, that regulate the application of the energization signal to the pump 34. The trigger 46 is selectively depressed to regulate both the on/off state of the pump 34 and the rate at which the pump is actuated. Also not illustrated in FIG. 1 is the power source that supplies the energization signal to the pump 34. In some versions of the invention this power supply may be a battery pack. This battery pack may be internal to or remote from the handpiece 32. Alternatively a console may function as the power supply.

A tip assembly 48 extends forward from the handpiece 32. Tip assembly 48 includes both a discharge tube 50 and a suction tube 52. The discharge tube 50 is in fluid communication with the outlet port of the pump 34. The suction tube 50 extends parallel to the discharge tube 42. Suction tube 52 is, at the end adjacent the handpiece 32, connected to a suction line 54. In some, but not all, versions of this invention, the suction line 54 is partially housed within the handpiece 32. In some but not of the versions of the invention wherein the suction line 54 is within the handpiece, the portion of the line within the hand piece is a rigid tube. External to the handpiece, suction line 54 is generally a flexible line. The rearwardly extending portion of the suction line 54 is connected to a suction source.

Both tubes 50 and 52 extend approximately the same distance forward of the handpiece 32. A spray shield 56 surrounds the open distal ends of both the discharge tube 50 and the suction tube 52. Here, "distal" is understood to mean towards the target site to which the solution is applied. "Proximal" means away from the target site to which the solution is applied.) Spray shield 56 has an open distal end 58. This end of the spray shield 58 is the portion of the lavage system 30 that is pressed against the site to which the basic or blended lavage solution is applied. In some, but not all, versions of the invention spray shield 58 is removable from the tip assembly 48.

Figure 6:
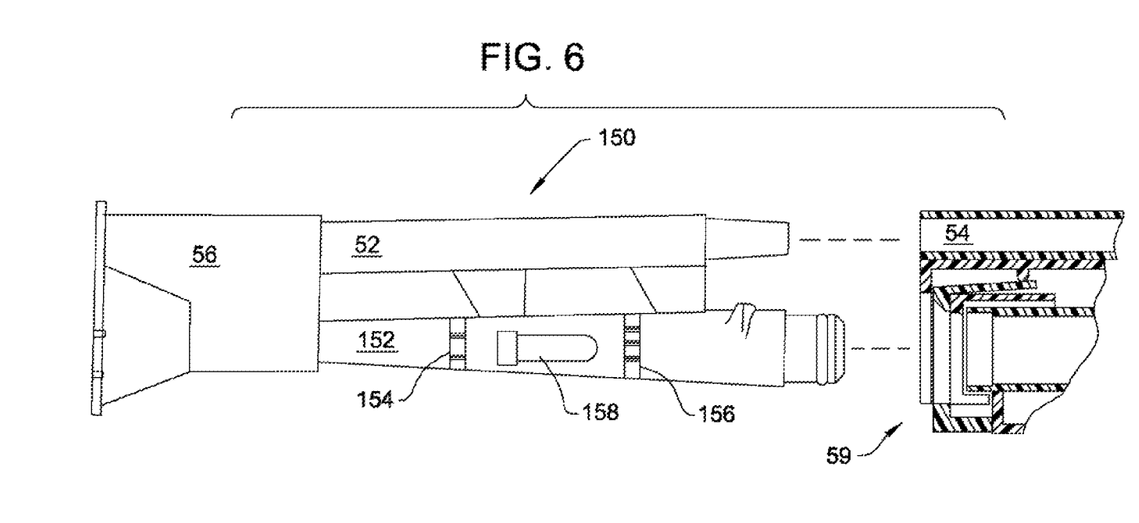
FIG. 6 is a cross sectional view of another alternative tip assembly that can be used to construct another alternative lavage system of this invention.

In many versions of the invention, tip assembly 48 is removably attached to the handpiece 32 by a lock assembly 59 (FIG. 6). One such lock assembly that can be used to so secure the tip assembly 40 to the handpiece is described in the incorporated-by reference U.S. Pat. No. 6,471,668. The exact structure of the assembly that allows the tip assembly to be replaced, including being replaced during a procedure, is not relevant to this invention.

Figure 2A:
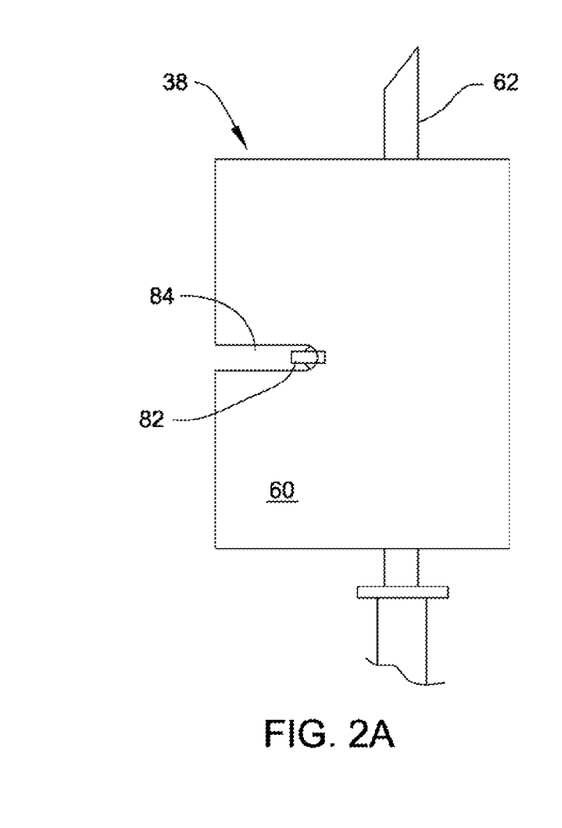
FIG. 2A is a plan view of the cartridge of one lavage system of this invention.
Figure 2B:
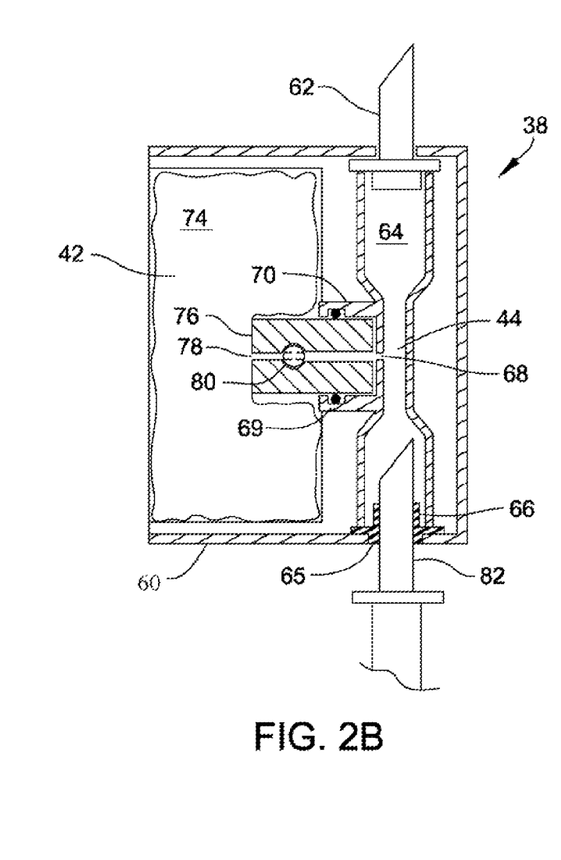
FIG. 2b is a cross sectional view of the cartridge of FIG. 2A; perspective view of an alternative tip assembly of this invention capable of delivering an additional compound with the primary lavage solution.

FIGS. 2A and 2B provide a detailed view of cartridge 38. The cartridge 38 has a body 60 typically formed from a rigid plastic. A spike 62 extends rearwardly from the proximal end of the cartridge body 62. The spike 62 is the component of the cartridge 38 that is constructed for removable coupling to the basic solution-containing bag 36. Not illustrated is the bore internal to spike 62 through which the basic solution flows from the bag 36. A venturi tube 64 disposed inside cartridge body 62 extends forward from the spike 62. Venturi tube 64 includes opposed wide diameter proximal and distal sections (sections not identified). The tube proximal section is the section that receives the flow from spike 62. Between the proximal and distal sections there is a middle section (not identified) with a diameter less than that of proximal and distal sections. The tube is constructed so that the proximal section tapers down into the middle section and the middle section tapers outwardly to the distal section. The void space within the middle section functions as the cartridge mixing chamber 44. Cartridge body 62 is formed with an opening 65 in which the free end of the tube distal end is seated. A plug 66 is seated in the open distal free end of the venturi tube 64.

Venturi tube 64 is formed with an opening 68 that projects radially outwardly from the narrow diameter center section. The venturi tube 64 is also formed to have a tube-shaped collar 70 that extends outwardly from the tube middle section. Collar 70 extends around opening 68. An O-ring 69 is fitted in collar 70. The O-ring 69 is seated in a notch formed in the inner wall of the collar 70 so that O-ring is located in the portion of the collar relatively close to the venture tube opening 64.

The cartridge reservoir 42 is formed by an envelope 74 of flexible material. In one version of the invention, envelope 74 is a bag formed of transparent plastic such as polyurethane, PVC or silicone. The envelope 74 has an opening, not identified, from which a neck 76, formed from a rigid plastic, extends. Neck 76 is fitted into the opening and bonded to the material forming the envelope so there is a hermetic seal between the envelope 74 and the neck. The neck 76 is formed to have an axially extending through bore 78 that leads from the envelope 74. Flow through bore 78 is regulated by a control valve 80 mounted to the neck 76. Specifically, the valve 80 includes a rotating valve body (not identified) that seated in a cylindrical valve chamber that intersects bore 78. The control of the extent to which the valve 80 is open is established by a control tab 82 integral with the valve body. The control tab 82 is located outside of the cartridge body 60.

Envelope 74 and neck 76 are removably attached to the cartridge body 60. To accomplish this mating, the cartridge body is formed so that the side of the body opposite the end in which the venturi tube 64 is seated is open. The front face of the body 60 is formed with a slot 84. Slot 84 extends from the open side of the body. The body 60 is formed so that slot 84 is linearly aligned with collar 70. Slot 84 is dimensioned to accommodate the stem section of the valve that extends between the valve body and control tab 82.

Lavage system 30 of this invention is prepared for use by taking the following steps. A quantity of the therapeutic agent that is be blended with the basic lavage solution is added to the envelope 74. This step may be performed at a facility where the envelope-and-neck sub-assembly is manufactured. Alternatively, this step is performed at the medical facility at which the procedure is to be performed.

Once the envelope is filled with therapeutic agent, the envelope and neck are fitted into the cartridge body 60. Specifically, this sub-assembly is slide into the open side of the body. The stem of the valve 80 is slide in body slot 84. This sub-assembly is displaced so that neck 76 seats in body collar 70. More particularly, the neck 76 is seated in the seal until the forward end of the neck, the end downline of valve 80, is fitted within collar O-ring 69. The O-ring 69 thus establishes a seal between collar 70 and neck 76.

Cartridge 38 is then coupled, "spiked," to the bag 36 holding the basic lavage solution. The proximal end of the supply tube 40 is provided with its own spike, spike 82. Functionally spike 82 is identical to spike 62. Thus, spike 82 can be used to connect the supply tube 40 directly to bag 36. When cartridge 38 is integrated into the system, spike 82, instead, inserted into cartridge plug 66. When so employed, spike 82 thus establishes a fluid connection between the proximal end of venturi tube 64 and the handpiece supply line 40.

System 30 of this invention is now ready for use. Gravity initially causes fluid flow from the container 36, cartridge venture tube 64 and supply line 40 to the pump 34. Depression of trigger 46 results in actuation of the pump 34. The actuation of the pump 34 results in the discharge of solution out of the handpiece and through the tip assembly discharge tube 50 to the target site.

When the clinician wants to discharge a blended solution, a mixture of the basic solution and the therapeutic agent, valve 78 is at least partially opened. The flow of the basic solution through the venturi tube results in development of a low lateral pressure through the narrow middle section of the tube. This low pressure draws the therapeutic agent from in reservoir 42, through neck bore 78 and tube opening 68 into the mixing chamber 44. In the mixing chamber 44, the therapeutic agent combines with the basic solution to form a blended solution. This blended solution is what is discharged at the target site.

When the clinician decides it is appropriate to return to discharging just the basic solution from system 30, valve 78 is closed. This results in the termination of the draw of the therapeutic agent out of the reservoir 42.

Integrated lavage system 30 of this invention provides a means of selectively applying a blended solution to a target site. For procedures in which there is no requirement for a blended solution, there is no need to include the cassette 38 as part of the system; the supply line 40 is connected, spiked, directly to the bag 36. When the blended solution is required, the cartridge 38 is placed in line as described above. The presence of the valve means that for a given period of time, the blended solution can be applied to the target site. Then, when a return to the basic solution is required, valve 78 is closed. This results in the cessation of the draw of the agent into the fluid stream. Thus, one does not have to either use a second handpiece or switch between bags containing either the basic solution or the blended solution in order to sequentially apply the basic and blended solutions to the target site.

Still another feature of this invention, is that two or more cartridges 38 can be connected in series. This allows the clinician to sequentially apply different blended solutions to the site by simply setting the valves 78 associated with the individual cartridges.

Moreover, the envelope and neck sub-assembly of the cartridge 38 is removably coupled to the cartridge body 38. One advantage of this arrangement is that it is possible to provide individual versions of these sub assemblies that vary only in the diameter of their neck bores 78. Generally, the venturi tube 64 is constructed so that tube bore 44 will have a diameter greater than neck bore 78. The flow rate of the agent from the reservoir 42 is proportional to the diameter of neck bore 78. Accordingly, by providing envelope-and-neck sub-assemblies with different sized neck bores, one can provide control, in addition to the setting of valve 78 for regulating the quantity of therapeutic agent that mixes with the basic solution in order to form the blended solution. If further control is needed, a smaller orifice can be added near bore 78 to control the flow of the agent from reservoir 42.

Figure 3:
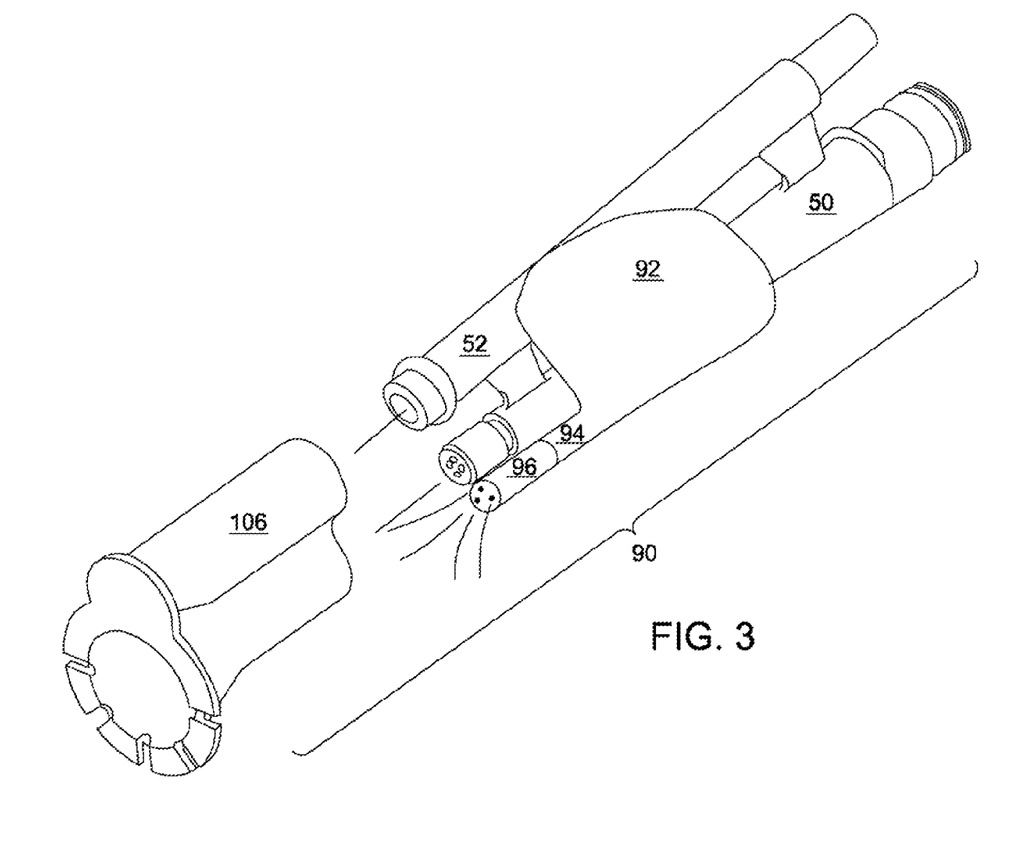
FIG. 3 is a perspective view of an alternative tip assembly that is used to construct an alternative lavage system of this invention.

FIG. 3 illustrates an alternative tip assembly 90 that can be used to assemble an alternative lavage system of this invention Tip assembly 90 includes the previously described discharge and suction tubes 50 and 52, respectively. Also part of tip assembly 90 is a pouch 92 formed from a flexible plastic such as polyurethane, PVC or silicone. Pouch 92 extends over both the discharge tube 50 and the suction tube 52. Adhesives or posts may be used to secure the pouch 92 to the other structural components of the tip assembly 90. Extending forward from and in fluid communication with pouch 92 is a second discharge tube 94. The second discharge tube 94 is secured to the tip assembly 90 to be adjacent to if not abut the first discharge tube, tube 50.

Figure 3A:
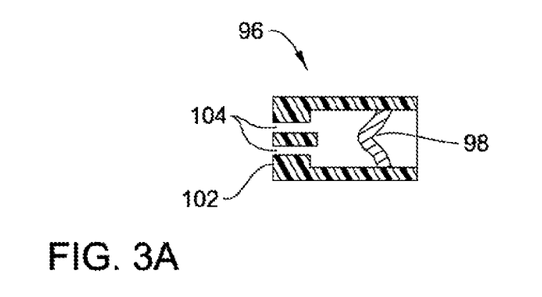
FIG. 3A is a cross sectional view of the head through which the therapeutic agent is discharged from the tip assembly of FIG. 3.

A head 96 is disposed over the distal end of the second discharge tube 94. The head 96, seen best in FIG. 3A, is in the form of a rigid tubular body. At the proximal end, duck billed-valve 98 is disposed inside the head. Valve 98 is provided to ensure that flow out of the head is one way, outwardly from the discharge tube 94. A cap 102 is disposed over the forward distal end of tube forming head 96. In some versions of the invention, the tubular portion of the head and cap 102 are formed as a single piece of plastic. One or more through bores 104 extend through the cap 102. Bores 104 are the openings through which therapeutic agent is discharged. The number of bores and their geometry is a function of the nature of the discharge pattern desired for the agent. For example, some caps 102 may be provided with a single bore 104. These caps are provided when it is desirable to discharge the agent in a jet. Other caps 102 may be provided with plural bores. These caps are provided with it is desirable to discharge the agent as diffused mist. It should be appreciated that there is a small space in the head between valve 98 and the proximally directed face of cap 102.

A spray shield 106 is disposed over the distal ends of the first and second discharge tubes 50 and 94, respectively and the suction tube 52. Forward of where tubes 50, 52, and 94 open into the spray shield 106 the shield is shaped to define an open-ended chamber 108. Spray shield 106 is formed so that the diameter of the chamber increases distally forward of where the discharge tubes 50 and 94 open into the chamber.

Tip assembly 90 is used as a substitute for tip assembly 48. When it is desirable to apply a therapeutic agent using tip assembly 90, pouch 92 is initially filed with the agent through the open end of the discharge tube 94. Head 96 is then fitted over the open end of the discharge tube 94. Spray shield 106 is fitted over the forward ends of the tubes 50, 52 and 94. Tip assembly 90 is fitted to handpiece 32.

Generally, the system of this invention is then used in a manner similar to that how a conventional lavage system is used. When the clinician wants to apply a basic lavage solution, trigger 46 is depressed so as to actuate the pump 34. When the clinician wants to dispense the therapeutic agent, pouch 92 is squeezed. The pressure applied to the pouch 92 forces the agent out of the pouch and through the discharge tube 94. The pressure is also sufficient to open up the valve 98. Downstream of valve 98 the agent flows out of the head cap bores 104. It should be appreciated that it may be necessary to squeeze the pouch 92 a number of times to first build up a head of agent in the void space between the valve 98 and the head cap 102.

This version of the lavage system can be used to dispense three different types of solution at the target site. As mentioned above, the system can be used to discharge the basic solution alone. Alternatively, by squeezing the pouch while leaving the pump 34 off, the system can be used to discharge therapeutic agent alone. Finally, by simultaneously actuating the pump 34 and squeezing the pouch, the system can be used to apply a blend of the agent and the basic solution.

Moreover, when employing this version of the invention, prior to the start of the procedure, plural tip assemblies 90 may be prefilled with agent. Depending on the nature of the procedure, the individual pouches 92 may be filled with different agents. Thus, in a first part of the procedure, when it is desirable to apply a soap to the target site, a first tip assembly with the pouch 92 filled with soap is attached to the handpiece 32. In a later stage of the procedure, it may be desirable to provide a bone growth enhancer to the site. At this time, the second tip assembly 90, with a bone growth-filled pouch 92, is attached to the handpiece 32.

It should be understood that the foregoing is directed to two versions of the lavage system of this invention. Other constructions of the lavage system are possible.

Figure 4:
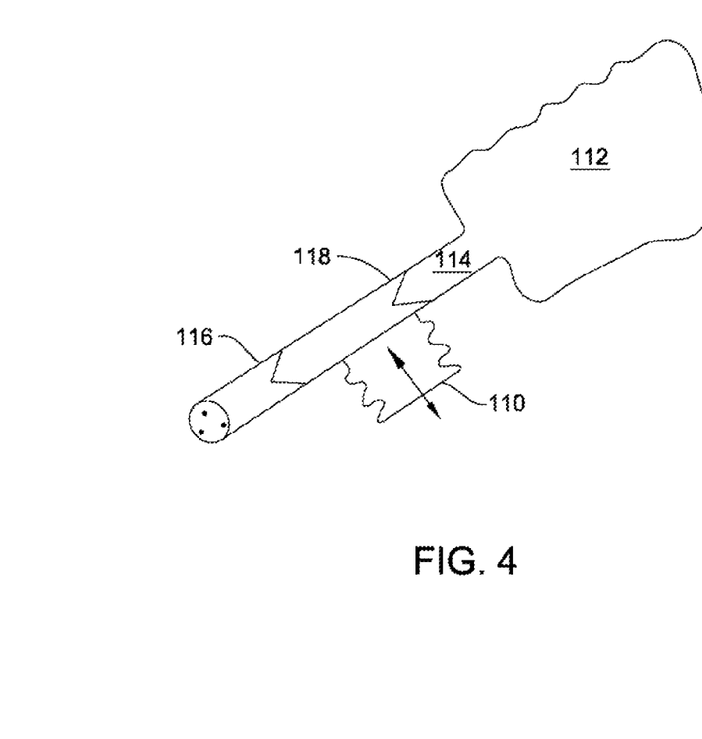
FIG. 4 is a diagrammatic illustration of an alternative therapeutic agent reservoir and discharge assembly for attachment to the tip assembly of this invention.

For example, in versions of the invention in which the reservoir in which the agent is stored is attached to the tip assembly, a small manually actuated bellows pump 110, seen in FIG. 4, may be mounted to the tip assembly. Here there is a reservoir 112 from which a discharge line 114 extends. Pump 110 is in series with the discharge line 114. One way valves 116 and 118, that allow flow in the distal direction are disposed in the discharge line 114 on either side of the pump. While not seen, it should be understood that in more versions of this embodiment of the invention, a vent may be provide in the reservoir 112 to allow the entry of make-up air.

Also, it should be understood that either pouch 92 or reservoir 112 may be removably attached to the associated tip assembly. In these versions of the invention, a one-way valve is often located at the head end opening of the pouch/reservoir. Such valve may perform the function of valve 98 or valve 118. This version of the invention would minimize the amount of components need to be replaced in order to supply more of or a different kind of therapeutic agent.

Figure 5:
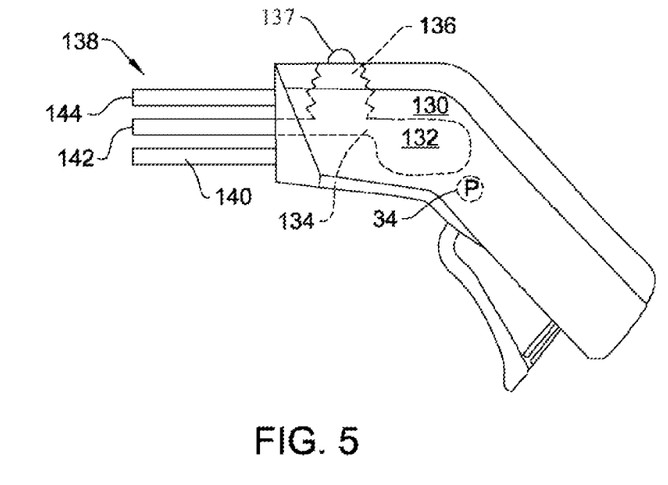
FIG. 5 depicts of how the therapeutic agent reservoir and discharge assembly are mounted internally to the handpiece in another version of this invention.

As seen in FIG. 5, an alternative handpiece 130 includes a built in reservoir 132 shown in phantom. A discharge line 134, also shown in phantom, extends from the reservoir. A manually actuated bellows pump 136, partially shown in phantom, in line with the discharge line 134, provides the force that draws the therapeutic agent out of the reservoir and forces the agent down the discharge line. Here, the pump 136 includes a head 137 that extends out of the body of the handpiece 130. Head 137 is the portion of the pump 136 that is manually depressed to cause the discharge of the therapeutic agent.

Partially shown in FIG. 5 is the alternative tip assembly 138 used with handpiece 130. Tip assembly has a first discharge tube 140. Discharge tube 140 connects to the outlet integral with pump 34. A second discharge tube, tube 142, connects to discharge line 134 internal to the handpiece 132. Tip assembly 138 also contains a suction tube 144 for connection to the suction line 54.

FIG. 6 illustrates a tip assembly 150 of this invention capable of dispensing a blended solution wherein the mixed in component is a solid or semi-solid material. Tip assembly 150 includes a discharge tube 152 and the previously described suction tube 52. Discharge tube 152 is similar to previously described discharge tube 50.

Internal to tube 152 are two longitudinally spaced apart screens 154 and 156 internal to the conduit defined by the tube. Tube 152 is formed with a slide panel 158 that exposes an opening between screens 154 and 156.

A lavage system using tip assembly 150 is used by placing a solid pellet, powder or semi-solid volume of the therapeutic agent in the tip between screens 154 and 156. During the lavage process, the lavage solution flow erodes the mass comprising the therapeutic agent. The screens 154 and 156 prevent the therapeutic agent from migrating down the conduit prior to being eroded or dissolved. The material eroded from the mass is carried downstream with the primary lavage solution so as to collectively form a blended lavage solution. It is this blended lavage solution that is then applied to the body site.

Thus, in this version of the invention the space in tube 152 between screens 154 and 156 can be considered the reservoir for the therapeutic agent.

Figure 7:
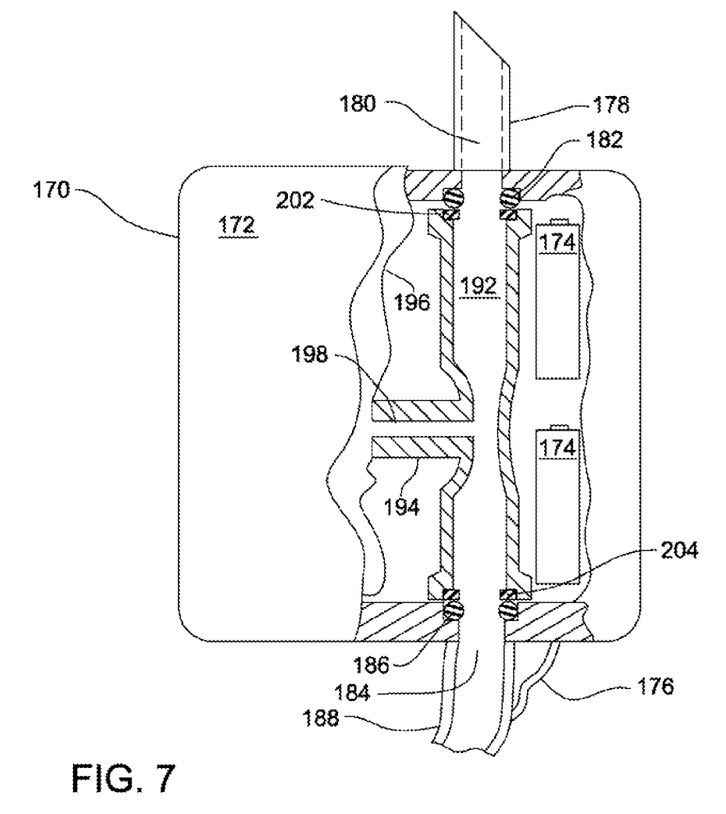
FIG. 7 is a partial cross sectional view of another cartridge of this invention.

An alternative cartridge 170 of this invention is illustrated by FIG. 7. Cartridge 170 includes a body 172. Body 172 is shaped to include one or more batteries 174, partially shown in phantom. Batteries 174 provide the energization signal used to actuate pump 34. A cable 176 extending from the body 172 carries the conductors used to establish the circuit connection between the pump 34 and the batteries 174.

A spike 178 extends proximally rearward from the top of the cartridge body 172. Spike 178 is used to establish a fluid connection to bag 36. The center bore of the spike 178 opens into a through hole 180 formed in the top panel of the cartridge body. An O-ring 182 is mounted to the top panel to extend around the distal end of hole 180. Not identified is the annular notch formed in the internal face of the body top panel around hole 182 in which the O-ring 182 is seated. Cartridge body 172 is further formed so that in the bottom panel there is second through hole 184 axially aligned with first through hole 180. An O-ring 186 is seated around through hole 180. Not identified is the annular notch formed in the inner face of body 172 around hole 184 in which O-ring 186 is seated. A supply tube 188, that substitutes for supply tube 40, is connected to the body 172 and extends forward the opening 180 to the handpiece 32 (FIG. 1).

Cartridge body 172 is further constructed to removable receive a venturi assembly in series with through holes 180 and 184. The venturi assembly includes a venturi tube 192. A side tube 194 is integrally formed with and extends laterally from the narrow waist section of venturi tube 192. A pouch 196 for holding a therapeutic agent is attached to the free end of side tube 194. Bore 198 extends axially through the side tube 194 to provide a fluid flow path from the pouch to the narrow diameter mixing chamber internal to the venturi tube. Not illustrated is a valve assembly that may be attached to side tube 194. This valve assembly, similar to valve 78 (FIG. 2B) is used to regulate fluid flow through the side tube.

Washer-shaped gaskets 202 and 204 are mounted to the opposed top and bottom ends of the venturi tube 192. Gasket 202 is seated in annular notch (not identified) that surrounds the open proximal end, top end, of the tube 192. Gasket 204 is seated in an annular notch (not identified) that surrounds the distal end, the bottom end, of the tube 192. In order to provide structural strength to the venturi tube 192 adjacent the gaskets, the opposed top and bottom ends of the tube are formed with outwardly extending flairs.

A lavage system with cartridge 170 is readied for use by first filing the pouch 196 with the therapeutic agent selected for application. The venturi tube assembly is then slid in the cartridge body 172. More particularly, the venturi tube assembly is positioned in the cartridge so that the tube 194 is disposed between the opposed holes 180 and 184. As a consequence of the dimensioning of the components, when the venture tube 194 is so positioned, tube gasket 202 presses against O-ring 182. This creates a seal around the top of the tube 194. Simultaneously, gasket 204 presses against O-ring 184. This creates a seal around the bottom of the tube 194.

When there is no need to blend a therapeutic agent with the lavage solution, a tube with a constant diameter is substitute for the venture tube assembly. This tube is provided with gaskets that perform the function of gaskets 202 and 204.

Cartridge 170 is then spiked to the bag 36. This embodiment of the lavage system of this invention is then available for use. Generally, this version of the system operates in the same general manner as version described with respect to FIG. 1.

Figure 8:
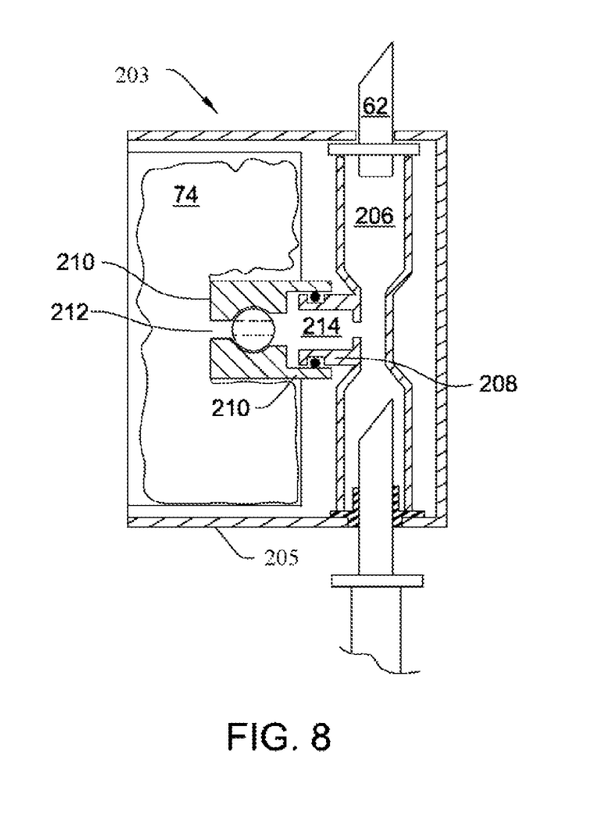
FIG. 8 is cross sectional view of another cartridge of this invention.

FIG. 8 illustrates still another cartridge 203. that can be placed in series between bag 36 and supply line 40. Cartridge 203 has a body 205 similar to the body of cartridge 38 and similar venturi tube 206. Here, venture tube 206 is formed with a side tube 208 that extends away from the narrow waist portion of the tube.

In this version of the invention, a head unit 210 extends away from the opening formed in envelope 74. The head unit 210 is formed to have first and second contiguous, coaxial and longitudinally extending bores 212 and 214. Bore 212 is the bore that leads away from the opening in envelope 74. Valve 80 is seated in bore 214. Bore 214 extends forward from bore 212, towards the venture tube 296. Bore 214 has a diameter greater than that of bore 212. More particularly, bore 214 has a diameter that allows side tube 208 to be fitted therein. An O-ring 216 disposed about the perimeter of the side tube 208 provides a seal between the outer surface of side tube 208 and the inner wall of head unit 210 that defines bore 214.

Figure 9:
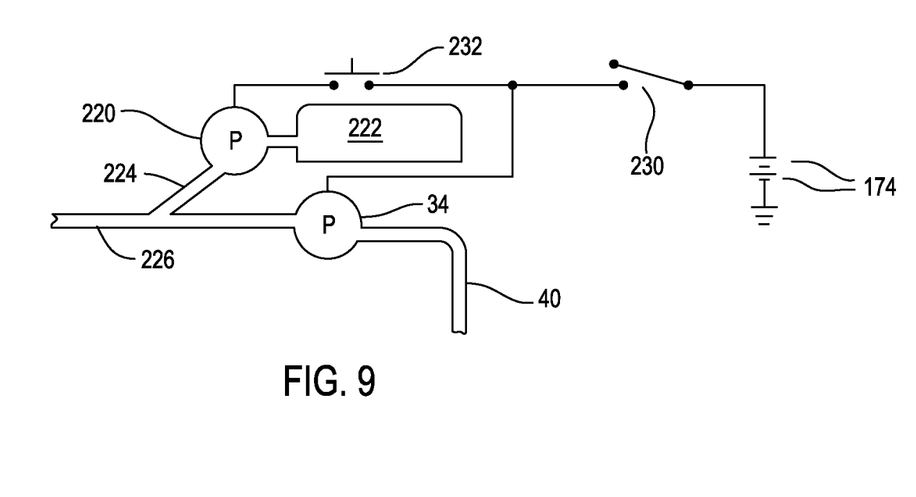
FIG. 9 is a block diagram of the components of an alternative lavage assembly of this invention for discharging a blended solution.

In some lavage systems of this invention, an electric pump may be used to draw the therapeutic agent from the reservoir so that it mixes with the basic solution to form the blended solution. FIG. 9 is a block diagram illustration of components of one such embodiment of this version of the invention. Seen in this Figure is pump 34 that pumps the basic solution form the supply tube 40. A pump 220 is provided to selectively draw the therapeutic solution from a reservoir 222. In some versions of this embodiment of the invention, pump 220 and reservoir 222 are contained in the system handpiece. This is what is depicted in FIG. 9. Thus pump 220 has an outlet line 224 that feeds into a discharge tube 226 that extends from pump 34. The point where these two conduits 224 and 226 meets can be considered the mixing chamber.

Figure 9A:
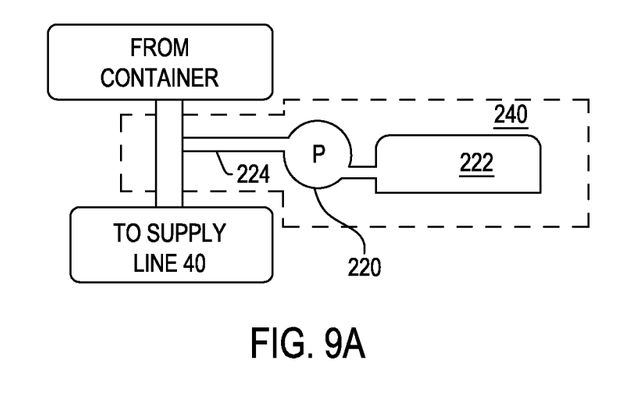
FIG. 9A is block diagram illustrating how the therapeutic agent pump of FIG. 9 can be installed in a cartridge.

In alternative embodiments of this version of the invention, pump 220 and reservoir 222 are contained in a cartridge 240 (shown in phantom similar to cartridge 38. In these embodiments of the invention, as depicted in FIG. 9A, the outlet line from pump 220 feeds into the supply line 40 connected to the inlet of pump 34.

In these versions of this invention first and second switches 230 and 232, respectively, are provided to control the actuation of the pumps 34 and 220. First switch 230 is connected between the power supply, represented by batteries 174, and pump 34. First switch 230 is normally open. The state of switch 230 the state of which is set by the actuation of trigger 46. First switch 230 is normally open. The first switch 34 is closed to actuate at least pump 34.

Second switch 232 is located between the first switch 230 and pump 220. Second switch is also a bi-state on/off switch. The second switch is a slide switch that can be set in a first state to connect to/or disconnect from pump 222. During periods in the procedure when only a basic lavage solution is required, the second switch 232 is set to disconnect pump 220 from the power supply. Then, when switch 230 is closed, the energization signal is only applied to pump 34. When discharge of the blended lavage solution is required, switch 232 is set to the connect mode. The subsequent depression of switch 230 results in the simultaneous application of an energization signals to and actuation of both pumps 34 and 220. The simultaneous actuation of both pumps 34 and 220 results in the discharge of the therapeutic agent into the stream of the solution discharged by pump 34. A blended solution is thus discharged from the system.

It should be appreciated that there is no requirement that all embodiments of the lavage system of this invention include each of the above-described features. Some of the described features may not be present in each of the described embodiments of the invention. Thus, in some instances the lavage system of this invention may not include a suction unit for drawing discharged solution away from the target site.

Also, various features from the different versions of the invention may be combined. Thus, one could provide a version of the invention that includes cartridge 38 or cartridge 170 with one of the tip assemblies 90 or 150. Likewise, handpiece 130 may be combined with other versions of the invention.

The components of the invention may also vary. For example, components other than spikes may be used to connect the cartridges to container of lavage solution or the supply line to the cartridge.

Likewise it should be understood that the switches of FIG. 9 are only exemplary, not limiting. In some versions of the invention the switch that applies the energization signal to pump 34 may actually be a potentiometer type switch or a rotary switch. In these versions of the invention, switch state is controlled by the extent to which trigger 46 is actuated. In these versions of the invention, the switch may be part of a double throw switch assembly. Here the second switch of the assembly is the switch that controls the application of the energization signal to therapeutic agent pump 220. Second switch 232 is still provided to control whether or not, when the trigger is depressed, pump 220 is to be actuated. This second switch of the double throw switch assembly may be a variable switch having a setting that is a function of trigger setting. This type of switch is provided when it is desirable to control the pumping rate of pump 220. Alternatively, this second switch is a single pole variety. This type of switch is useful when it is desirable to actuate the pump 220 at a given rate as soon as trigger 46 is depressed and the rate at which the pump 220 can be actuated can stay constant.

Similarly, there is no requirement that in all versions of the invention that pump 34, the pump that discharges the lavage solution, be located in the handpiece. In some versions of the invention, this pump be in the cassette or a remote console.

Furthermore, it should be appreciated that the therapeutic agents which the system of this invention can be used to discharge should be interpreted to cover essential all compounds that could provide a benefit to the patient. Thus, therapeutic agents include compounds used to manage wounds and surgical sites, enhance debridement, manage infection and contamination, modify the remodeling of hard tissue, improve the healing of both hard and soft tissue, and reduce pain. Types of therapeutic agents other than soap that can be blended with the lavage solution include, but are not limited to, analgesics, antibiotics, anesthetics, narcotics, antiseptics, bactericidals, antibiotics, steroids, emulsifiers, surfactants, photo sensitizers, enzymes, bisphosphonates, bone morphogenic proteins (BNPs), growth factors, synthetic peptides, vasorestrictors and pharmaceutical preparations that foster tissue regeneration and/or minimize scaring. Therapeutic agents can be in the form of a solution, powder, monolith or gas. In the case of a gaseous state therapeutic agent a flow regulator is provided between the reservoir and mixing chamber to ensure the proper ratio of the liquid, the basic solution to the gas, the therapeutic agent, Thus, in one exemplarily procedure using the lavage system of this invention, us a debridement enhancer such as a soap, one may want to first lavage the site with a blend of soap and lavage solution followed by a final lavage with saline. Using certain antiseptics, bactericidals, and photo sensitizers, one may want to first debride/lavage the site with saline, followed by application of the therapeutic agent either independently or in combination with the standard lavage solution, and then clean the site with a final lavage utilizing the standard lavage solution. This may be desirable to minimize the potential toxic effects of certain residual therapeutic agents in the site. Alternatively, one may want to introduce the therapeutic either separately or blended with the base lavage solution as the final solution application to the site. This may be the best sequence of steps for compounds such as antibiotics, certain photo sensitizers, certain antiseptics, certain bactericidals, growth factors, bisphosphonates, bone morphogenic proteins, synthetic peptides, analgesics, anesthetics, and narcotics. This would be desirable for compounds that are more efficacious when present at the site for extended periods of time. These are only meant to be examples of different combination variants and why one would consider different application sequences. The most preferred mode of introduction will be dependent on the site, specific therapeutic compound, and therapeutic need.

Therefore it is the purpose of the appended claims to cover all such variations and modifications that fall within the true spirit and scope of this invention.

What is claimed is:

1. A tip assembly for a medical/surgical irrigator, the irrigator having a discharge head with an open end from which a pump internal to the irrigator discharges a lavage solution and a suction line having an open end through which a suction is drawn, said tip assembly having:
   a first discharge tube that has opposed proximal and distal ends, the proximal end shaped for fitting to the open end of the irrigator discharge head to receive solution discharged out of the irrigator pump, the distal end having an opening through which the solution is applied to a target medical/surgical site;
   a suction tube attached to said first discharge tube, said suction tube having opposed proximal and distal ends, the suction tube proximal end being open and being shaped to be fitted to the open end of the irrigator suction line, the distal end having an opening through which suction drawn through the suction tube is applied to the target medical/surgical site, wherein said suction tube is attached to the first discharge tube so that, the fitting of the proximal end of said first discharge tube to the irrigator discharge head results in the fitting of said suction tube to the irrigator suction line;
   a coupling feature integral with said first discharge tube or said suction tube configured to cooperate with an complementary coupling feature integral with the irrigator so that, when the coupling features cooperate, the coupling features releasably hold said first discharge tube and said suction tube to the irrigator; and
   a reservoir attached to said first discharge tube or said suction tube configured to store a therapeutic agent, said reservoir including: an outlet directed to the target medical/surgical site; and a reservoir pump that is separate from the irrigator pump that is actuated independently of the irrigator pump, said reservoir pump being a manually operated pump that, when actuated, discharges therapeutic agent from said reservoir out of the reservoir outlet to the target medical/surgical site.

2. The tip assembly of claim 1, wherein a second discharge tube separate from said first discharge tube extends from said reservoir, said second discharge tube being formed with the reservoir outlet and said reservoir pump is formed from flexible material that, when compressed, causes therapeutic agent to be discharged through said second discharge tube and out the reservoir outlet.

3. The tip assembly of claim 1, wherein a second discharge tube separate from said first discharge tube extends from said reservoir, said second discharge tube being formed with the reservoir outlet and said reservoir pump is connected to said second discharge tube for pumping therapeutic agent from said reservoir, through said second discharge tube and out through the reservoir outlet.

4. The tip assembly of claim 1 wherein said coupling feature is a flange that extends outwardly from said first discharge tube or said suction tube.

5. The tip assembly of claim 1, wherein said coupling feature is integrally formed with said first discharge tube.

6. The tip assembly of claim 1, wherein at least one of said first discharge tube and said suction tube is provided with a seal that is separate from and extends around said tube for providing a barrier between said tube and the irrigator discharge head or the irrigator suction line.

7. The tip assembly of claim 1 further including a spray shield that extends forward from the distal end of said first discharge tube, the distal end of said suction tube and the reservoir opening, said spray shield shaped to define a chamber into which lavage solution from said first discharge tube and therapeutic agent from the reservoir are discharged and from which said suction tube draws a suction, the chamber having an opening that is applied over the target medical/surgical site.

8. The tip assembly of claim 1, wherein at least one of said first discharge tube or said suction tube is formed with a feature shaped to cooperate with a complementary feature integral with a spray shied so that the features can engage to hold the spray shield adjacent the distal end of said first discharge tube, the distal end of said suction tube and the reservoir opening.

9. The tip assembly of claim 1, wherein said suction tube is spaced from said first discharge and is connected to said first discharge tube by at least one web.

10. A tip assembly for a medical/surgical irrigator, the irrigator having a discharge head with an open end from which a pump internal to the irrigator discharges a lavage solution and a suction line having an open end through which a suction is drawn, said tip assembly having:
  a first discharge tube that has opposed proximal and distal ends, the proximal end shaped for fitting to the open end of the irrigator discharge head to receive solution discharged out of the irrigator pump, the distal end having an opening through which the solution is applied to a target medical/surgical site;
  a suction tube attached to said first discharge tube, said suction tube having opposed proximal and distal ends, the suction tube proximal end being open and being shaped to be fitted to the irrigator suction line, the distal end having an opening through which suction drawn through the suction tube is applied to the target medical/surgical site, wherein said suction tube is attached to the first discharge tube so that, the fitting of the proximal end of said first discharge tube to the irrigator discharge head results in the fitting of said suction tube to the irrigator suction line; and
  a pouch formed from flexible material that is attached to said first discharge tube or said suction tube so as to extend at least partially over at least one of said tubes, said pouch configured to store a therapeutic agent; and
  a second discharge tube that extends forward from said pouch that is in fluid communication with said pouch, said second discharge tube having at least one outlet opening adjacent the distal ends of said first discharge tube and said suction tube and being in fluid communication with said pouch so that the compression of said pouch results in the discharge of therapeutic agent through the second discharge tube toward the target medical/surgical site.

11. The tip assembly of claim 10, wherein said pouch extends at least partially over both the first discharge tube and the second discharge tube.

12. The tip assembly of claim 10, further including a coupling feature integral with said first discharge tube or said suction tube configured to cooperate with a complementary feature integral with the irrigator so that, when the coupling features cooperate, the coupling features releasably hold said first discharge tube and said suction tube to the irrigator.

13. The tip assembly of claim 12, wherein said coupling feature is integrally formed with said first discharge tube.

14. The tip assembly of claim 10, wherein at least one of said first discharge tube and said suction tube is provided with a seal that is separate from and extends around said tube for providing a barrier between said tube and the irrigator discharge head or the irrigator suction line.

15. The tip assembly of claim 10, further including a spray shield that extends forward from the distal end of said first discharge tube, the distal end of said suction tube and the second discharge tube outlet opening, said spray shield shaped to define a chamber into which lavage solution from said first discharge tube and therapeutic agent from the reservoir are discharged and from which said suction tube draws a suction, the chamber having an opening that is applied over the target medical/surgical site.

16. The tip assembly of claim 10, wherein at least one of said first discharge tube or said suction tube is formed with a feature shaped to cooperate with a complementary feature integral with a spray shied so that the features can engage to hold the spray shield adjacent the distal end of said first discharge tube, the distal end of said suction tube and the second discharge tube outlet opening.

17. The tip assembly of claim 10, wherein said pouch is adhesively secured to at least one of said first discharge tube or said suction tube.

18. The tip assembly of claim 10, wherein said suction tube is spaced from said first discharge and is connected to said first discharge tube by at least one web.

* * * * *